(12) United States Patent
Branco

(10) Patent No.: US 6,520,975 B2
(45) Date of Patent: Feb. 18, 2003

(54) KIT FOR ENDOVASCULAR VENOUS SURGERY

(76) Inventor: Antonio Carlos Branco, R. Dr. Jose Augusto de Queiroz, 256, Sao Paul, CEP 05670-030 (BR)

( * ) Notice: Subject to any disclaimer, the term of this patent is extended or adjusted under 35 U.S.C. 154(b) by 0 days.

(21) Appl. No.: 09/899,315

(22) Filed: Jul. 5, 2001

(65) Prior Publication Data

US 2001/0047170 A1 Nov. 29, 2001

Related U.S. Application Data

(63) Continuation-in-part of application No. PCT/IB00/00378, filed on Feb. 2, 2000.
(60) Provisional application No. 60/163,684, filed on Nov. 5, 1999, provisional application No. 60/148,242, filed on Aug. 11, 1999, and provisional application No. 60/144,800, filed on Jul. 21, 1999.

(51) Int. Cl.[7] ............................. A61B 17/22; A61B 1/00
(52) U.S. Cl. ..................... 606/159; 600/104; 600/114
(58) Field of Search ............................ 606/41, 45, 46, 606/47, 48, 49, 50, 159

(56) References Cited

U.S. PATENT DOCUMENTS

| 5,022,399 A | | 6/1991 | Biegeleisen | |
|---|---|---|---|---|
| 5,599,299 A | | 2/1997 | Weaver et al. | |
| 5,634,935 A | * | 6/1997 | Taheri | 604/96.01 |
| 5,707,389 A | | 1/1998 | Louw et al. | |
| 5,797,947 A | * | 8/1998 | Mollenauer | 606/108 |
| 5,817,013 A | * | 10/1998 | Ginn et al. | 600/101 |
| 5,843,104 A | | 12/1998 | Samuels | |
| RE36,043 E | * | 1/1999 | Knighton | 600/101 |
| 5,902,316 A | * | 5/1999 | Mollenauer | 600/207 |
| 5,916,233 A | * | 6/1999 | Chin | 606/190 |
| 6,042,538 A | * | 3/2000 | Puskas | 600/114 |
| 6,071,232 A | * | 6/2000 | Knighton et al. | 600/104 |
| 6,169,916 B1 | | 1/2001 | West | |
| 6,352,544 B1 | * | 3/2002 | Spitz | 606/159 |
| 6,390,098 B1 | * | 5/2002 | LaFontaine et al. | 128/898 |

* cited by examiner

Primary Examiner—Linda C. M. Dvorak
Assistant Examiner—Kenneth Schopfer
(74) Attorney, Agent, or Firm—McDermott, Will & Emery

(57) ABSTRACT

The instant invention provides endoluminal methods and devices for the removal of anatomical structures such as vascular structures under endoscopic visualization of the process from within the anatomical structure or surgical region of interest. The present invention allows a surgeon to perform these procedures using a small number of small incisions.

The present invention provides an elongated flexible endoscopic guide which may be passed through the lumen of an elongate vessel or structure, such as for example, the saphenous vein from an entry veinotomy to an exit veinotomy. The guide provides passageways for a variety of surgical devices: an endoscope for viewing the surgical regions of interest, a cautery device and other surgical tools for performing ligation and other surgical procedures, and phleboextractor for removing elongate structures. A porous flexible drain can be deployed to provide pharmacological agents or collecting fluid at the surgical site. In the preferred embodiment, the device is used to care for chronic venous insufficiency, varicose saphenous vein segments, venous insufficiency, and varicose veins, by removal of those veins or segments.

30 Claims, 13 Drawing Sheets

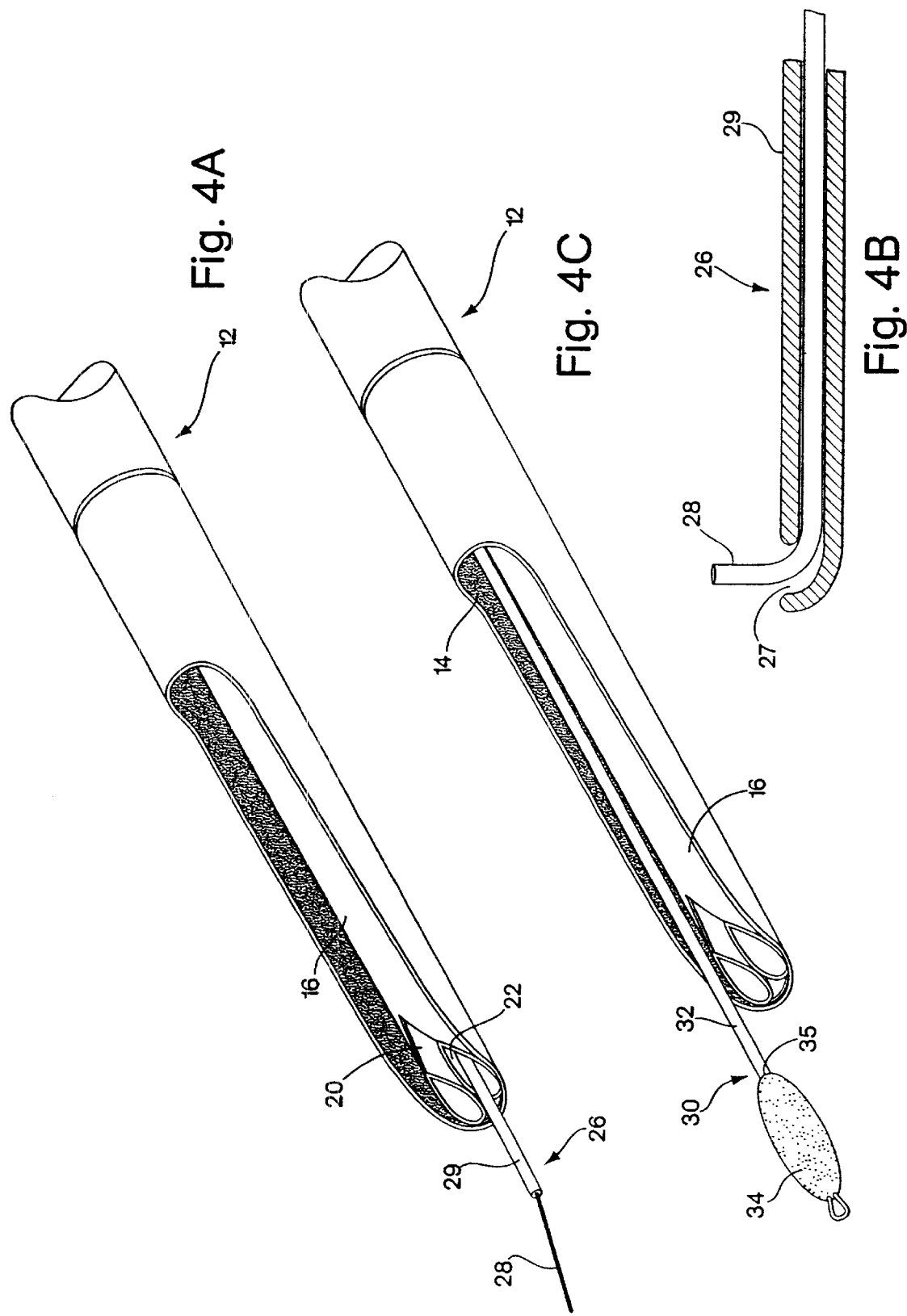

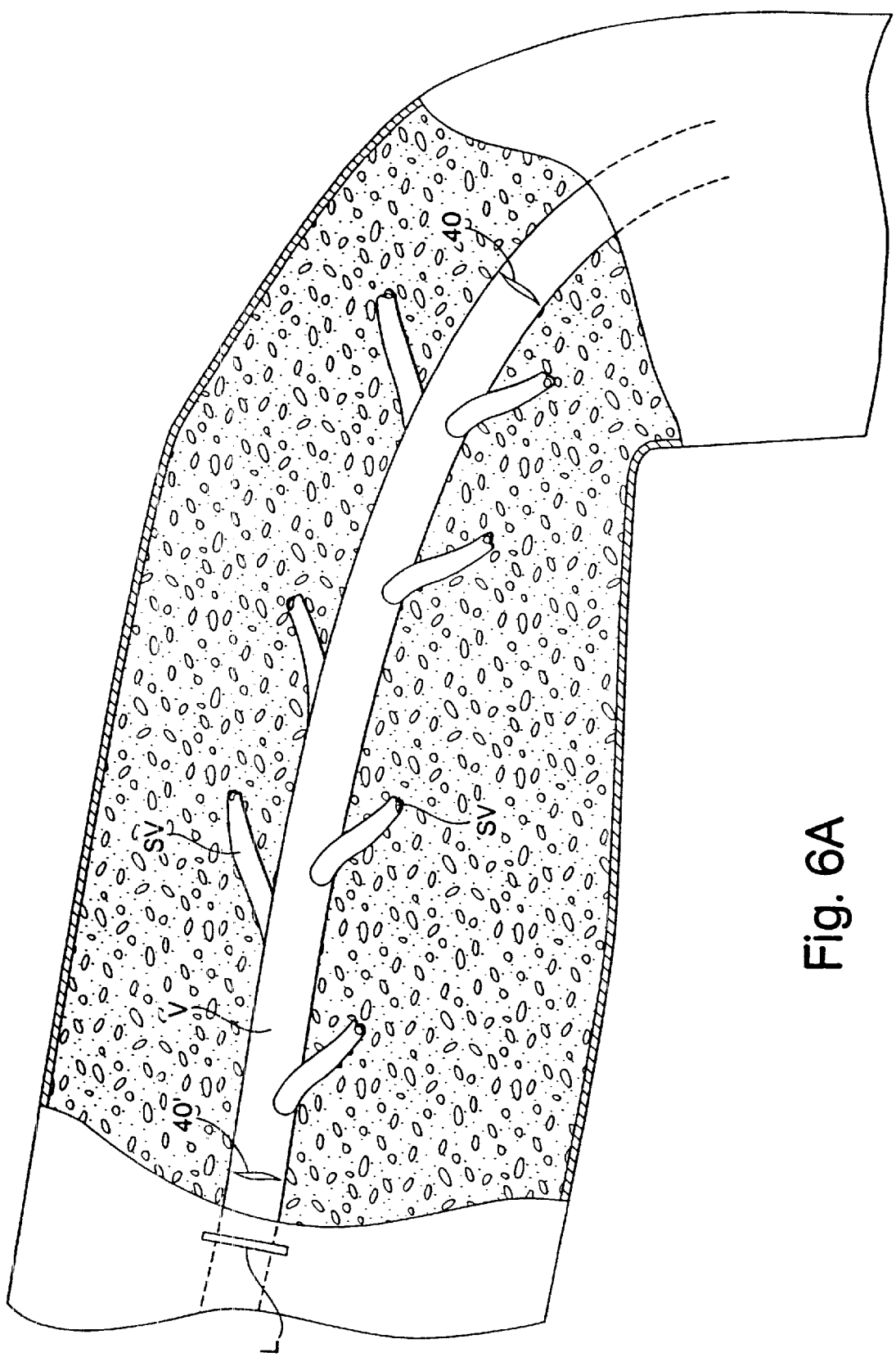

KIT FOR ENDOVASCULAR VENOUS SURGERY

CROSS REFERENCES TO RELATED APPLICATIONS

This application is a continuation-in-part of PCT Application No. PCT/IB00/00378 filed Feb. 2, 2000, which claims priority to Brazilian Patent Application No. PI 9900481-0 filed Feb. 4, 1999, and claims the benefit of U.S. Provisional Application Ser. No. 60/144,800 filed Jul. 21 1999, U.S. Provisional Application Ser. No. 60/148,242 filed Aug. 11, 1999, and U.S. Provisional Application Ser. No. 60/163,684 filed Nov. 5, 1999.

FIELD OF THE INVENTION

This invention pertains to methods and devices for endovascular surgery, in particular to methods and devices for treating, repairing and removing blood vessels.

BACKGROUND OF THE INVENTION

Varicose veins are swollen, tortuous veins with abnormally functioning valves. It is a common, progressive condition that usually affects the veins of the leg, and results in pain, muscle cramps and a feeling of heaviness in the legs. For mild cases, elevation of the legs or elastic stockings can help relieve the symptoms. For more severe cases, particularly where there is significant impairment and disruption of quality of life, surgical intervention can be warranted.

Numerous surgical procedures and devices have been developed for the treatment of varicose veins. One method for treating varicose veins is injection therapy, whereby a sclerosing agent is injected into varicose veins, which irritates the inside walls of the veins, causing blockage of blood flow. In another technique for varicose veins in the leg, known as vein stripping, the saphenous vein is excised. Initially, a first incision is made near the ankle and a second incision is made near the groin (or knee). Through those incisions full veinotomies are made at opposite ends of the segment of vein to be removed, isolating that segment from the patient's circulatory system. Branch veins connected to the venous segment are ligated, usually through access gained through small incisions. A wire is then introduced through the first incision and into the distal (upstream) end of the vein. The wire is fed into the vein until the lead end of the wire exits from in the proximal (downstream) end of the vein segment. Next, a disk with a diameter slightly larger than the vessel segment diameter is attached to the wire at the lead end, and the surgeon slowly retracts the wire from the distal end of the vein segment, so that the disk engages the proximal end of the vein segment and "pushes" the proximal end of the vein segment toward the distal end and in due course out the first incision.

U.S. Pat. No. 5,022,399 to Beigeleisen describes an endoluminal device for treating varicose veins. The device consists of a modified venoscope with a multilumen catheter. The venoscope provides a fiber optic direct viewing apparatus in one lumen, a wire mounted, rotatable ultrasonic blood flow direction and velocity monitoring device, and an injection system in other lumens for administering sclerosing agents or cauterizing side branches. This patent discloses cauterizing or sclerosing varicose veins. U.S. Pat. No. 5,707, 389 to Luow, also provides a method for cauterizing side branches of blood vessels using directed cauterizing catheters employed under endoscopic control. However, both the '399 and '389 patents teach methods and devices which leave the diseased vein in the patient, allowing the later development of varicose veins from currently normally functioning side branches or from recanalization of the original vessel.

U.S. Pat. No. 5,843,104 to Samuels, discloses a stripper head that is sutured to the end of a vein segment to be removed. The instrument is then retracted back through the vein segment, so that the vein segment is inverted and drawn to an exit port. Other similar stripper heads are known in the art. Because these stripper head devices apply tension to a small area of tissue, the vessel can tear and not be completely removed. Forceps and other tools, or more incisions may be necessary to complete the venous removal process.

In one form, the kit also provides a cautery device that extends through one lumen provided within the guide. The preferred cautery device includes an elongated flexible electrically non-conductive tubular sheath which surrounds a flexible elongated electrically conductive cauterizing element. Under operator control, the cauterizing element may be driven to extend beyond the end of the sheath and the guide. In one form, the cauterizing element has shape memory and is L-shaped when unconstrained, and is constrained to have the shape of one of the sheaths when retracted therein. Alternately, the sheath may have a deflector surface at its exit to direct the cauterizing element (and the sheath, in some forms) along a path angularly offset from the principal axis of the guide. The orientation of the cauterizing element about the sheath axis is operator controllable from the proximal end of the guide. With this configuration, selective cauterization of branch vessels may be effected.

The kit further includes an elongated phleboextractor extending between a proximal end and a digital end thereof. The phleboextractor is insertable through a lumen of the guide, and has an extractor device at its distal end. The extractor device is adapted for frictionally engaging tissue external to the end of the guide when the distal end of the phleboextractor extends beyond the distal end of the guide. The extractor device can be a balloon which can be selectively inflated to a shape having a diameter greater than that of the guide and deflated. The balloon may be elastic or inelastic. The outer surface of the balloon can be smooth, roughened or possess regions of both types of surfaces to provide secure engagement between the balloon and surrounding tissue. The phleboextractor is adapted so that upon deployment with its distal end beyond the guide, and its balloon inflated, the proximal end of the phleboextractor may be pulled from the first incision at the proximal end of the guide, with its distal end (and the extractor) device dragging with it the vein segment.

The kit may further include tubular a drain of porous flexible material which is adapted to be inserted into the second incision and connected to the phleboextractor at its distal end and be drawn into the surgical area as the There exists a need for a device that allows visualization and location of the diseased veins, ligation of the diseased veins, and if necessary, removal of the main vein in a manner that causes the least trauma to the surrounding area, with minimal surgical intervention.

SUMMARY OF THE INVENTION

It is an object of the present invention to provide a kit for performing endovascular venous surgery. The kit provides an elongated flexible multilumen tubular guide extending along a guide axis from a proximal end to a distal end thereof. The distal end of guide is preferably beveled. In one embodiment the tubular guide has an outer diameter in the approximate range of 4–8 mm. This range is preferred for varicose vein treatment. In other embodiments, other diameters may be used, for example in the range of 1–12 mm, or greater, in some cases.

The tubular guide has at least a first lumen and second lumen each extending along axes substantially parallel to the guide axis. Alternately, the guide has a single lumen which serves as a support and guide for at least one or more tubular structures. Such structures also extend along respective axes from a proximal end to distal end, with those axes being substantially parallel to the guide axis.

An angioscope is positionable in one of the lumens. The angioscope is capable of providing an image of a surgical region of interest exterior to the distal end of the guide. The angioscope includes an elongated image transfer element extending along its axis from a proximal end to a distal end, and generates at its proximal end an image representative. of a region adjacent to its distal end. The angioscope may be either fixedly or removably positioned with a lumen. In a preferred embodiment, the angioscope has an image sensor at the distal end for generating an electronic image signal representative of the region adjacent its distal end. The image signal is transferred to processing equipment at the proximal end. More preferably, the angioscope is a fiber optic viewing device. phleboextractor is withdrawn through the first incision. The drain can be infused with pharmacological agents or collect wound drainage.

BRIEF DESCRIPTION OF THE DRAWINGS

The foregoing and other objects of this invention, the various features thereof, as well as the invention itself, may be more fully understood from the following description, when read together with the accompanying drawings, in which:

FIG. 4A is an oblique view of the guide of the kit of FIG. 1 showing a cautery device;

FIG. 4B shows a cross section of an alternate embodiment of the end of the cautery device;

FIG. 4C shows an oblique view of the guide of the kit of FIG. 1 showing a phleboextractor;

FIGS. 6A–F are perspective views illustrating the method of harvesting a vein using one embodiment of the invention;

DESCRIPTION OF THE PREFERRED EMBODIMENTS

The instant invention provides endoluminal methods and devices for the removal of anatomical structures such as vascular structures under endoscopic visualization of the process from within the anatomical structure or surgical region of interest. The present invention allows a surgeon to perform these procedures using a small number of small incisions. Because the surgeon has direct intraluminal observation of the vascular segments under resection, that process can be precisely performed to minimize trauma to the surrounding tissues, and with highly accurate identification of surrounding vessels and ligatures. This results in reduced intra- and post operative complications to the patient, and an improved cosmetic result.

Figure 1:
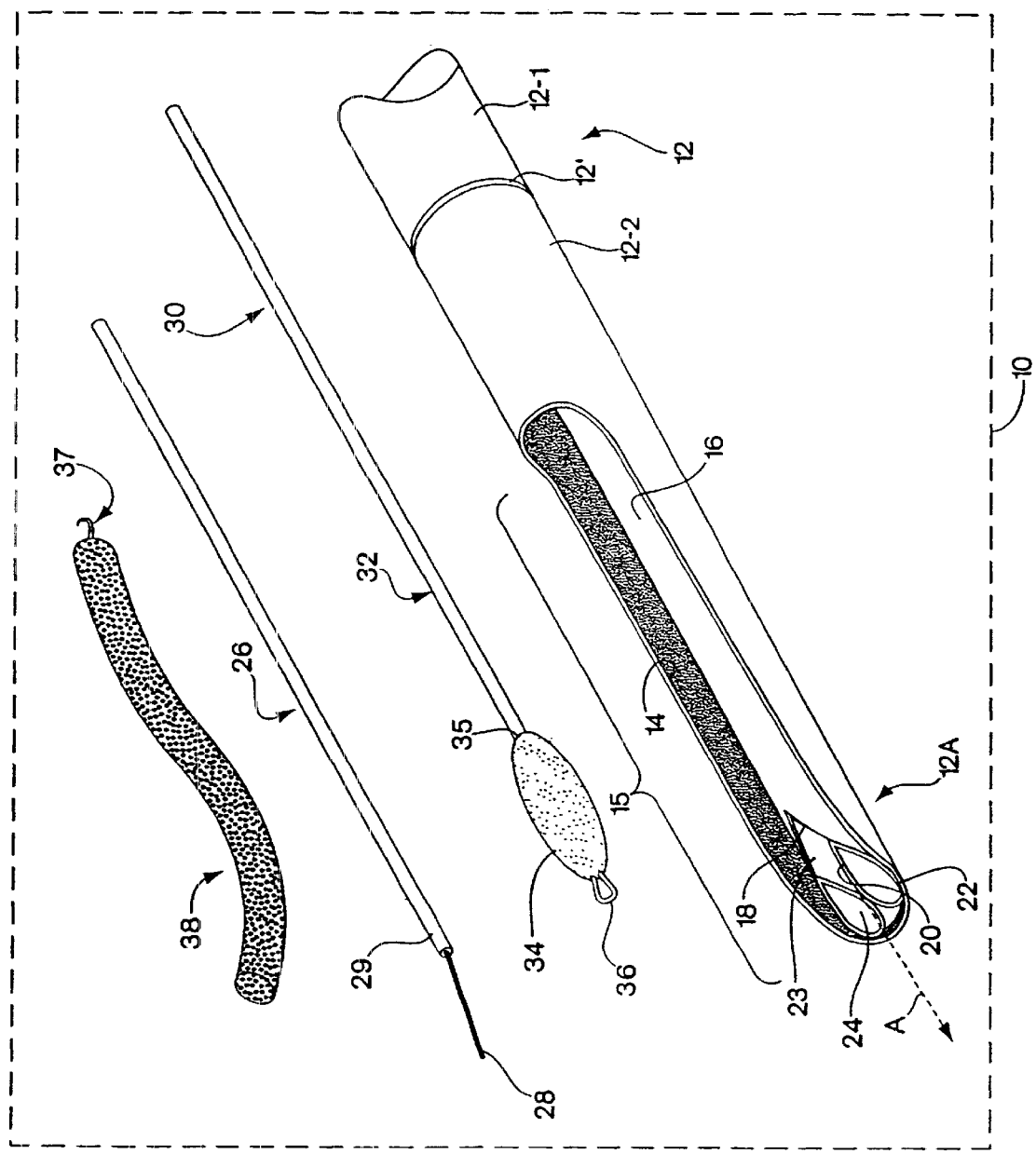
FIG. 1 is a perspective view of an endoscopic venous surgery kit according to the present invention.
Figure 2:
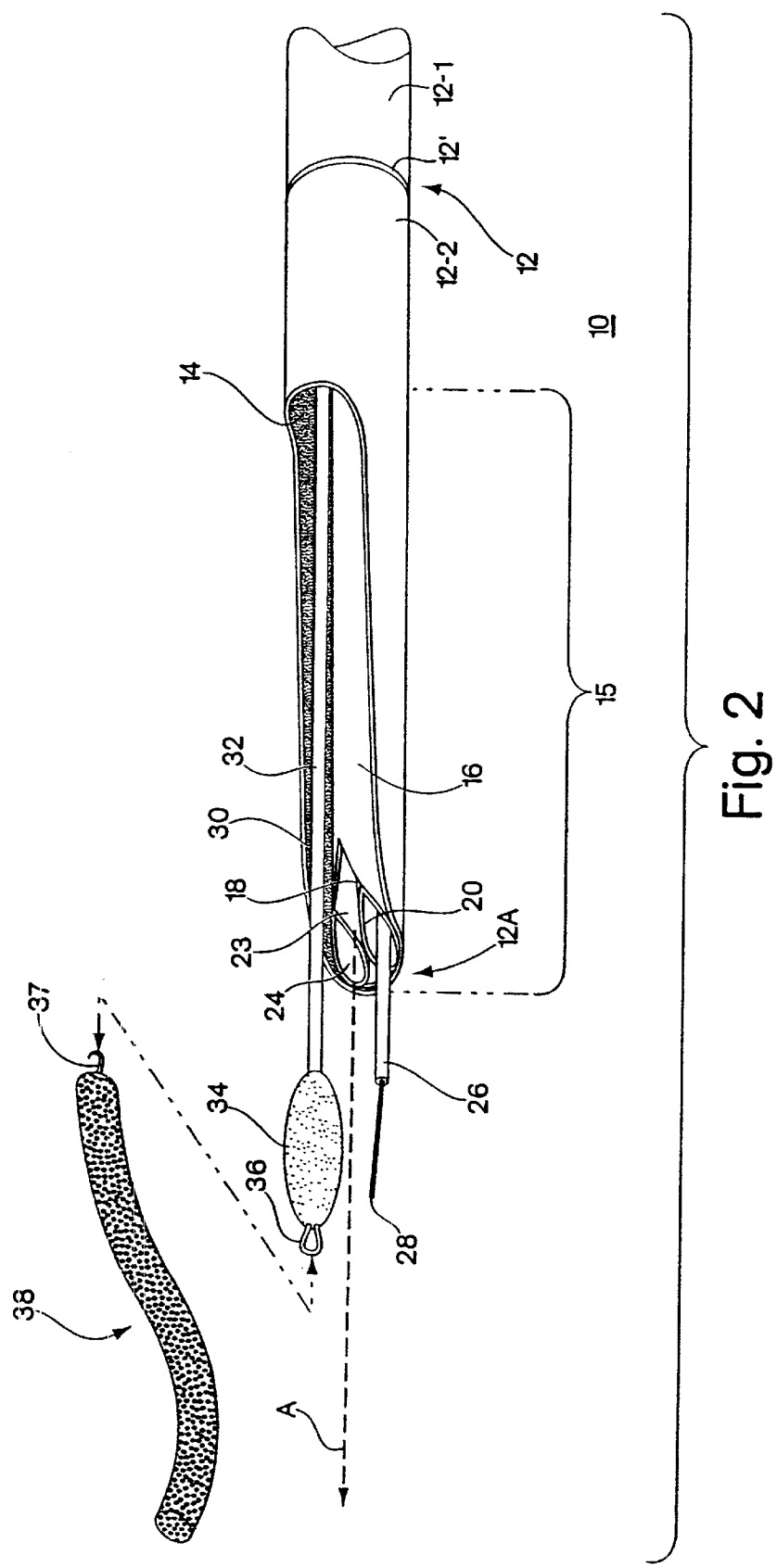
FIG. 2 shows the kit of the FIG. 1 and its components relative to each other as they are positioned for use.

FIGS. 1 and 2 show the preferred embodiment of endoscopic surgical kit 10. FIG. 1 shows the individual elements of the kit, whereas FIG. 2 shows the elements relative to each other as they are positioned for use. Briefly, the present invention provides an elongated flexible endoscopic guide 12 which may be passed through the lumen of an elongate vessel or structure, such as for example, the saphenous vein from an entry veinotomy to an exit veinotomy. As illustrated, the guide 12 has two parts 12-1 and 12-2, selectively joined at junction 12'. The proximal portion 12-1 is an elongated catheter portion, and the distal portion 12-2 is a replaceable tip portion.

The guide 12 provides passageways for a variety of surgical devices: an endoscope 24 for viewing the surgical regions of interest, a cautery device 26 and other surgical tools (not shown) for performing ligation and other surgical procedures, and phleboextractor 30 for removing elongate structures. A porous flexible drain 38 can be deployed to provide pharmacological agents or collecting fluid at the surgical site. In the preferred embodiment, the device is used to care for chronic venous insufficiency, varicose saphenous vein segments, venous insufficiency, and varicose veins, by removal of those veins or segments. The guide 12 is initially fed through a vein segment under intraluminal visual examination (via endoscope 24) by the surgeon. As the lead end of the guide 12 passes through the vein segment, the surgeon may deploy ligating and cauterizing devices through the guide 12 to effect ligation of side branches observed via the endoscope 24. When the distal end 12A of the guide 12 reaches the end of the vein segment, the surgeon may deploy an extractor 30 at the distal end 12A, and then withdraw the extractor 30 with the guide 12, thereby pulling out the vein segment. Other surgical techniques, discussed below, are also considered to be within the scope of the invention.

The endoscopic surgery kit 10 comprises an elongated, flexible, endoluminal guide 12 which is an elongated tube having a lumen 14 extending along guide axis A from the proximal end (not shown) to the distal end 12A of guide 12. Guide 12 is disposed about an inner cannula 16, which in turn is disposed about a tool cannula 20 and an endoscope cannula 23. Guide 12 is formed from flexible material, which allows it to easily deform to permit non-damaging passage through the tortuous paths of blood vessels and particularly, varicose veins. At its proximal end (not shown), guide 12 is coupled to various devices, electronics and the like, that, among other activities, provide light sources, actuate and focus viewing devices, and activate and operate the various endoscopic tools used therethrough. Guide 12 may have one or more couplers to those devices, such as conventional fluid couplers and mechanical linkages.

Figure 3:
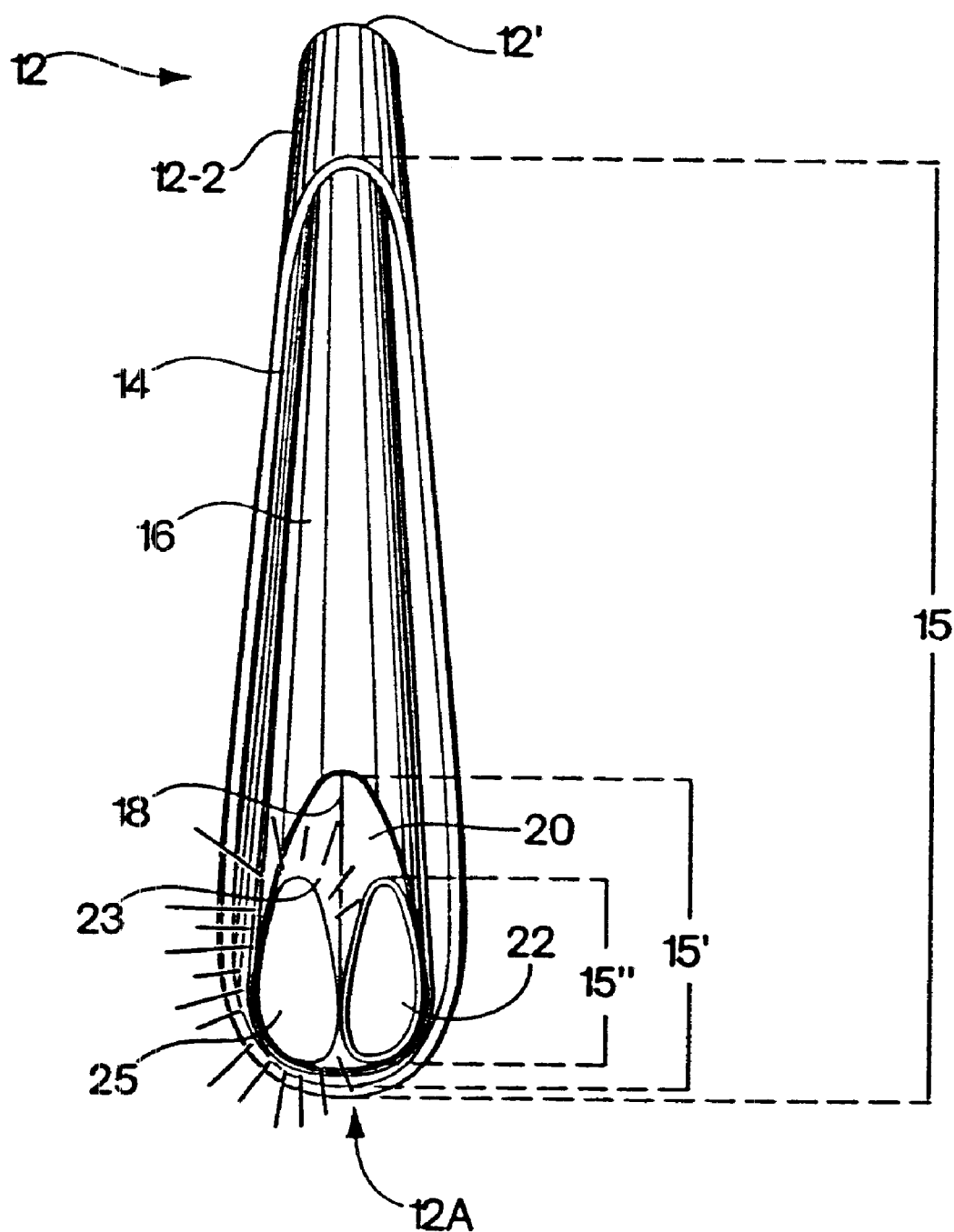
FIG. 3 is an end elevation view of the guide of the kit of FIG. 1.

As seen in FIG. 3, the distal region 15 of guide 12 is beveled, allowing lumen 14 to communicate with the exterior environment surrounding guide 12, or it may be tubular to the distal tip 12A. The bevel geometry provides an increased viewing area for endoscope 24, which enhances the ability to manipulate endoscopic tools inside the confines of the vessel or guide 12 and allows the guide to be inserted into veins without the need for a guide wire.

Cannula 16 is an elongated flexible shaft of slightly smaller diameter than guide 12. Cannula 16 also extends along an axis between its proximal end and a distal end, substantially parallel to axis A and inside a guide lumen 14 within guide 12. Cannula 16 may extend and retract under operator control within lumen 14. Cannula 16 has a central lumen 18, which optionally may be divided into a plurality of longitudinally running lumens along axis A. At its proximal end, cannula 16 may also connect to various control mechanisms. Distal region 15' is beveled providing increased access area exterior to endoscopic device. Distal region 15' may have the same bevel geometry as region 15, or it may be formed at a less oblique angle as the bevel on distal region 15.

Like cannula 16, tool cannula 20 is a hollow tube of flexible material extending along an axis substantially parallel to axis A. At its proximal end, tool cannula 20 may connect with cannula 16, or it may branch from it at junctions or connectors as needed for the operation of the endoscopic tools which pass through its lumen 22. The distal region 15" of tool cannula 20 may be beveled in a manner fashion to distal regions 15 or 15'. Cannula 16 and tool cannula 20 may be separate flexible tubes that can slide proximally and distally to one another and guide 16 along longitudinal axis A. In an alternative embodiment, guide 12 has multiple lumens integrally formed within lumen 14 which form one or both of cannula 16 and tool cannula 20.

Cannula 23 provides passage for endoscope 24. Endoscope 24 may be any endoscopic visualization device known in the art; a fiber optic device is the preferred embodiment. At its proximal end, endoscope 24 is connected to adjustment devices for powering, focusing, advancing and retracting the endoscope, and various viewing devices, such as eye pieces or monitors, video cameras, recording devices and the like. At its distal end, it communicates with the environment in the surgical region of interest, and may terminate in lenses, housings and the like.

Endoscope 24 functions in the lumen 25 of cannula 23 in parallel with various endoscopic tools that pass through lumen 18. Alternately, endoscope 24 may travel in a separated sub-lumen from the endoscopic tools in lumen 18, when cannula 16 has multiple lumen, or endoscope 24 may pass through a separate sheath, isolating it from the tools within the cannula. In the preferred embodiment, endoscope 24 travels within lumen 25 of cannula 23 and the endoscopic tools pass through lumen 22 of tool cannula 20, which is rests within cannula 16 and may extend or retract within it.

FIG. 4A shows an embodiment where the guide 12 has a beveled tip and a dual channeled cannula 16. In that embodiment, cautery device 26 extends and retracts within lumen 22 of tool cannula 20. In one form, cautery device 26 is an elongated, flexible, electrically non-conductive sheath 29 which surrounds a flexible elongated electrically conductive cauterizing element 28, and extends beyond the end of sheath 29. At its proximal end, cautery device 26 has power and control means. Cautery device 28 may have shape memory, for example, being generally L-shaped when unconstrained, allowing it enter off-axis side vessels. When retracted and constrained, cautery device 26 returns to the shape of lumen 22. Alternately, the sheath may have a deflector surface at its exit forming a port 27 to guide the cauterizing element into side branches (FIG. 4B). In other embodiments, cautery device 26 can be any cautery device known in the art, such as electrical, thermal, laser, or ultrasonic energy.

FIG. 4C shows the distal end of an embodiment, again having a beveled distal end and including a cannula 16, with a phleboextractor 30. Phleboextractor 30 extends and retracts within lumen 14 of endovascular guide 12 exterior to cannula 16. Phleboextractor 30 in a preferred form, comprises hollow tube 32 which extends longitudinally from a proximal end to a distal end which communicates with mouth 35 of balloon 34. In this embodiment, the tube 32 passes in the region between the top (as shown) of guide 12, and the top (as shown) of cannula 16. At its proximal end, tube 32 is connected to control mechanisms, such as valves, stopcocks and the like, and fluid or gas reservoirs which provide means to expand (inflate) or retract (deflate) balloon 34 by the infusion of gas or fluid.

Figure 5A:
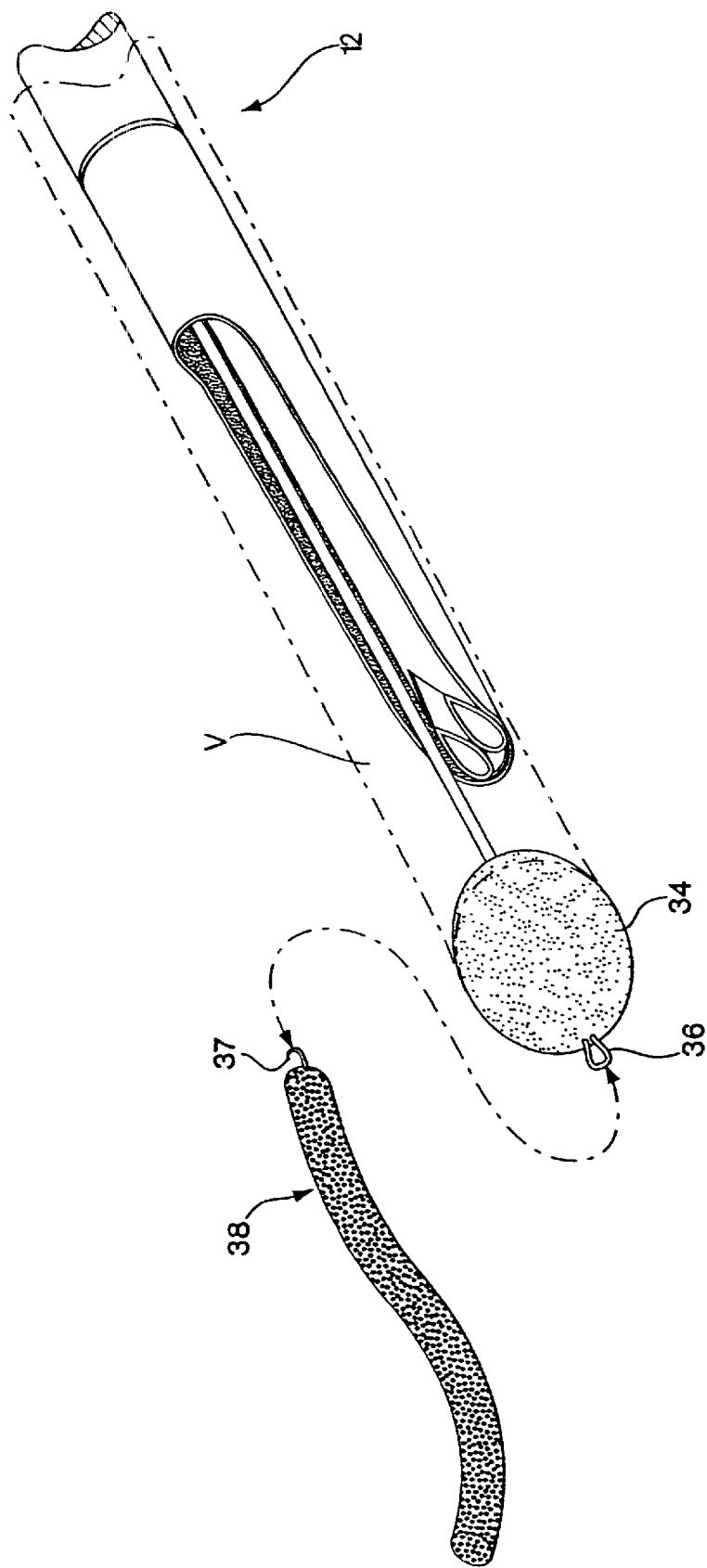
FIG. 5A is a perspective view of the kit of the invention with the balloon extractor deployed to engage a vein (V) to be removed.

When deflated, balloon 34 is retracted against tube 32 in a manner to occupy as small a volume as possible to ease navigation of the phleboextractor through lumen 14. When it is expanded, it occupies a larger volume than the diameter of the vessel being harvested or trauma area being occluded by it to form a seal (FIG. 5A). When inflated, balloon 34 can be elongate, conical, bell shaped or round, and is sized to be suitable for and to accommodate the surgical region of interest. The outer surface can be smooth, textured, frictioned in some way or possess areas with different surface textures. It is formed from materials known in the art for manufacturing angioplasty-type balloons, such as elastic or inelastic materials, or it can have regions of both materials. Similarly, the balloon may be formed from one or more sheets of material, with each sheet being formed from elastic, non-elastic or both types of material. Balloon 34 may also be formed as one piece or from multiple joined pieces. Balloon 34 is connected to tube 32 at balloon mouth 35 by means well known in the art for securing angioplasty-type balloons to inflation tubes, such as adhesives, and fusion welding processes. Alternately, the balloon 34 can be rigid and detachaly coupled to tube 32 with a form as illustrated in FIG. 5A.

Optionally, balloon 34 may have a connecting member 36 attached to its most distal end. Connection member 36 may be a hook, ring, loop or other such type of device for attaching other devices thereto. Connecting member 36 is formed from materials suitable for use within the body: surgical grade stainless steel, biocompatible polymers and the like. It may formed as an integral part of balloon 34, or may formed separately and attached to balloon 34 by means known in the art suitable for their respective materials.

Drain 38 provides means to infuse pharmacological agents such as analgesic, anesthetic, or antibiotic solutions to the region of interest after the endoscopic procedure. Drain 38 also serves in draining blood and other fluid that collect in the surgical site. Drain 38 is formed from flexible, porous, biocompatible material. Such material may be additionally a bio-absorbable polymer, (i.e, a polymer that dissociates and dissolves in situ). Drain 38 can have a round, elongate or flat cross section, and has a diameter and length suitable for the site of intended use. Drain 38 has a connecting member at one end that facilitates releasable attachment to balloon 34 at connecting member 36. Various configurations are contemplated for connecting members 36 and 37, the preferred is a hook and ring shape, where either member may be round, elongate, or substantially squared.

Figure 5B:
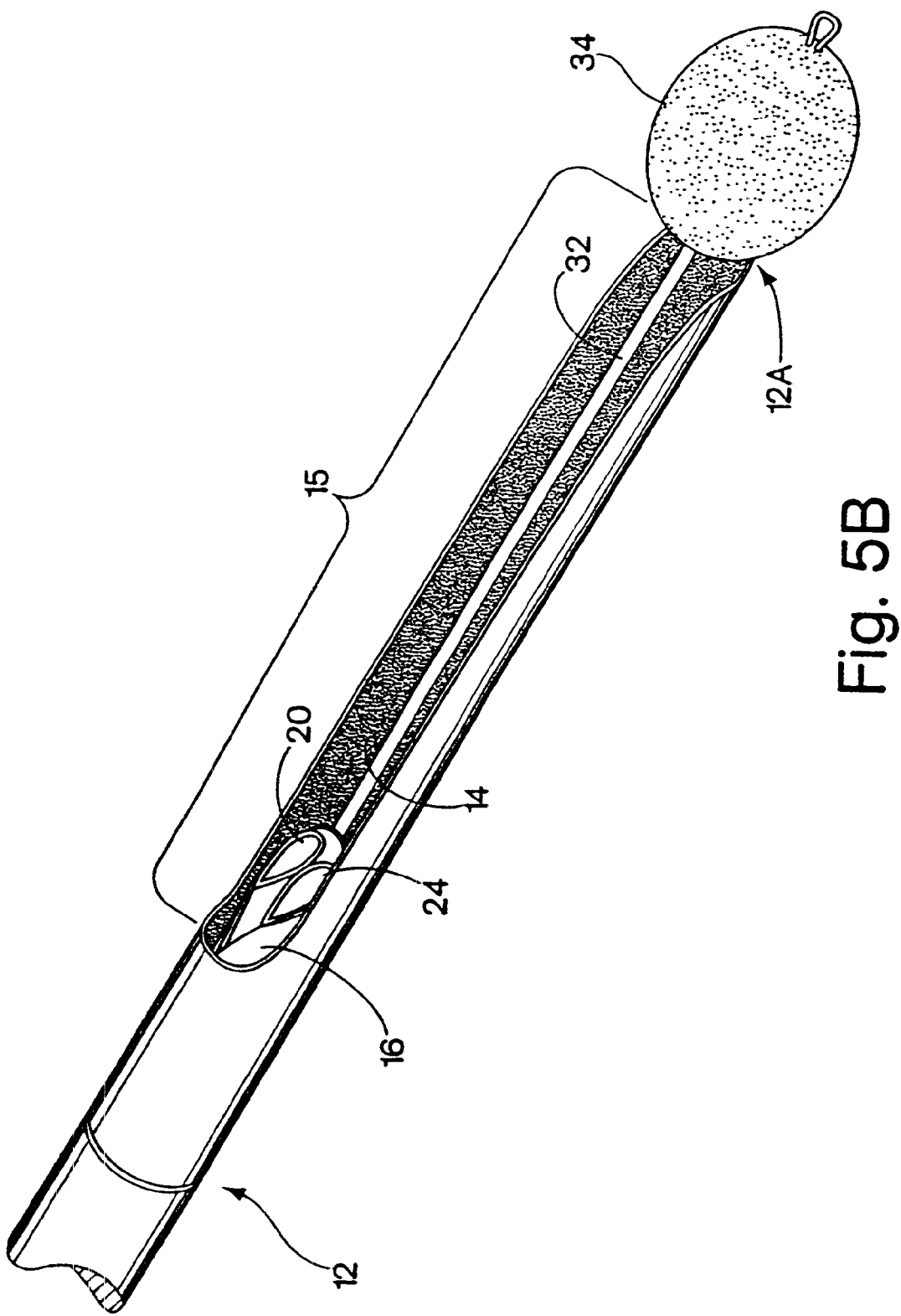
FIG. 5B shows a perspective view of an alternate configuration of the invention.

FIG. 5B shows yet another embodiment of guide 12. In this form, the assembly is substantially the same as that shown in FIG. 4C, except that tube 32 passes through the region between the bottom (as shown) of cannula 16 and the bottom (as shown) of guide 12. In one form, cannula 16, endoscope 24, and tool cannula 20 can be longitudinally retracted from tip distal tip 12A. In some forms, they can be retracted approximately 20 cm. This configuration provides a greater range of visualization area between endoscope 24 and the inflated balloon 34.

Figure 6B:
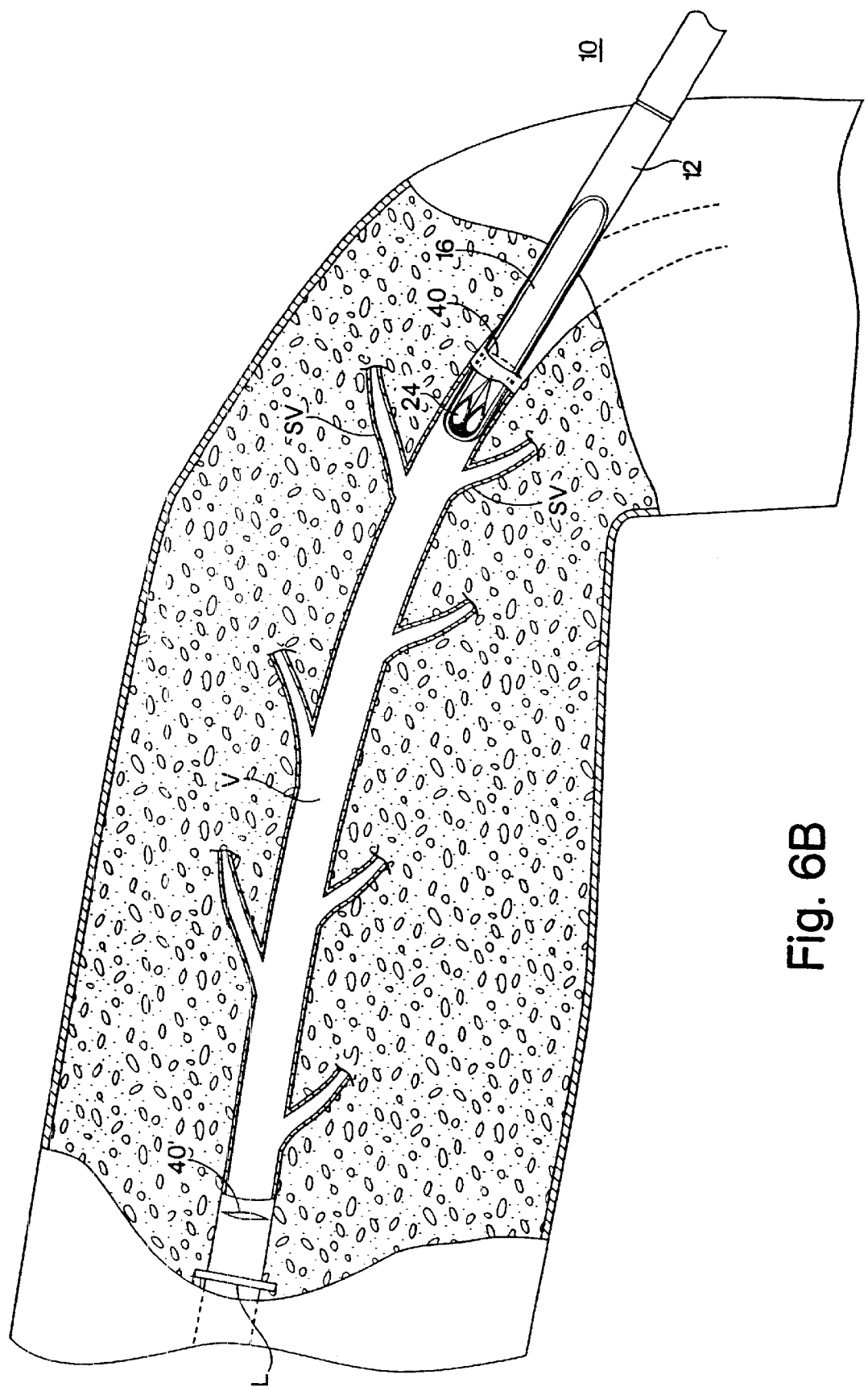
Figure 6C:
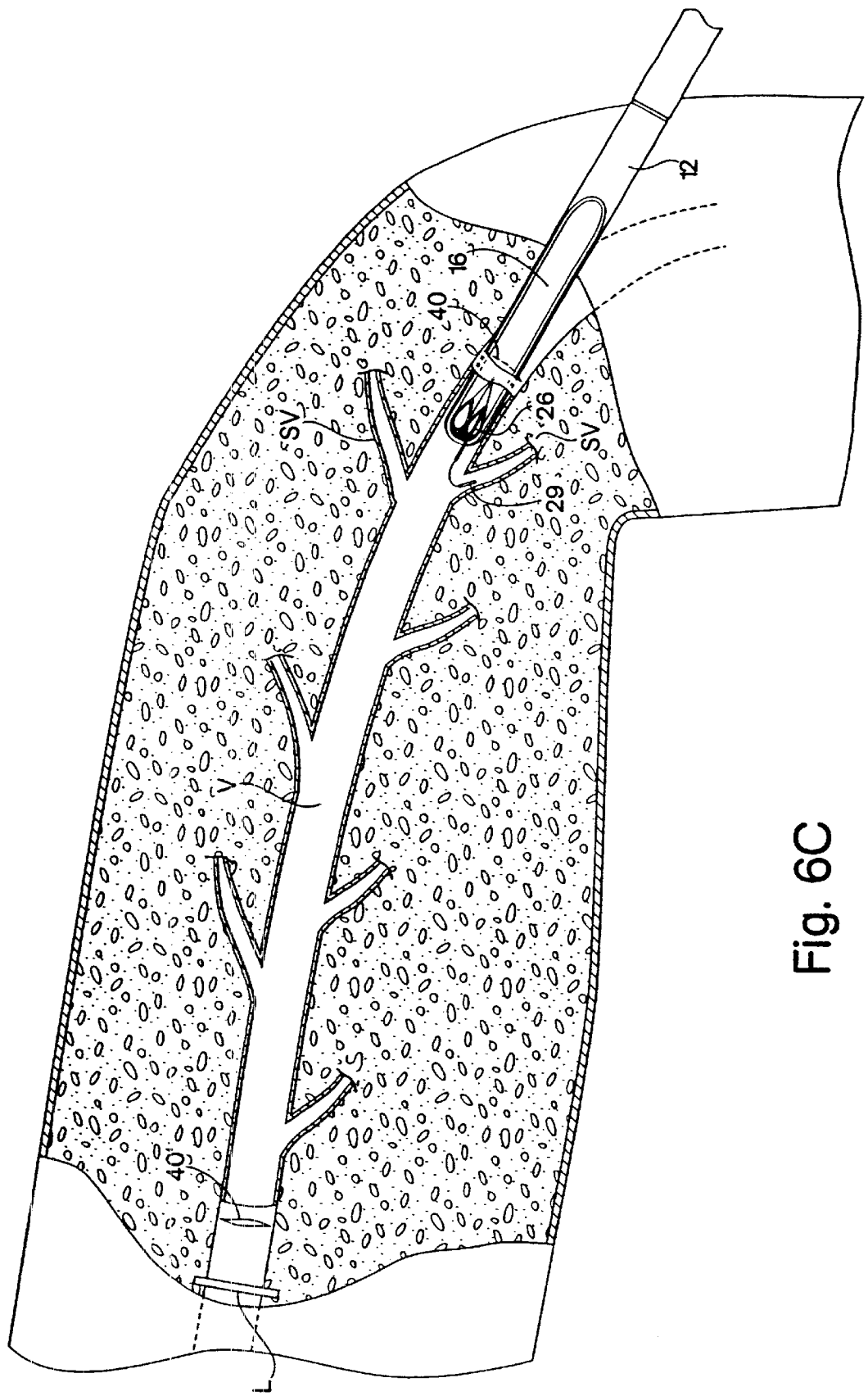
Figure 6D:
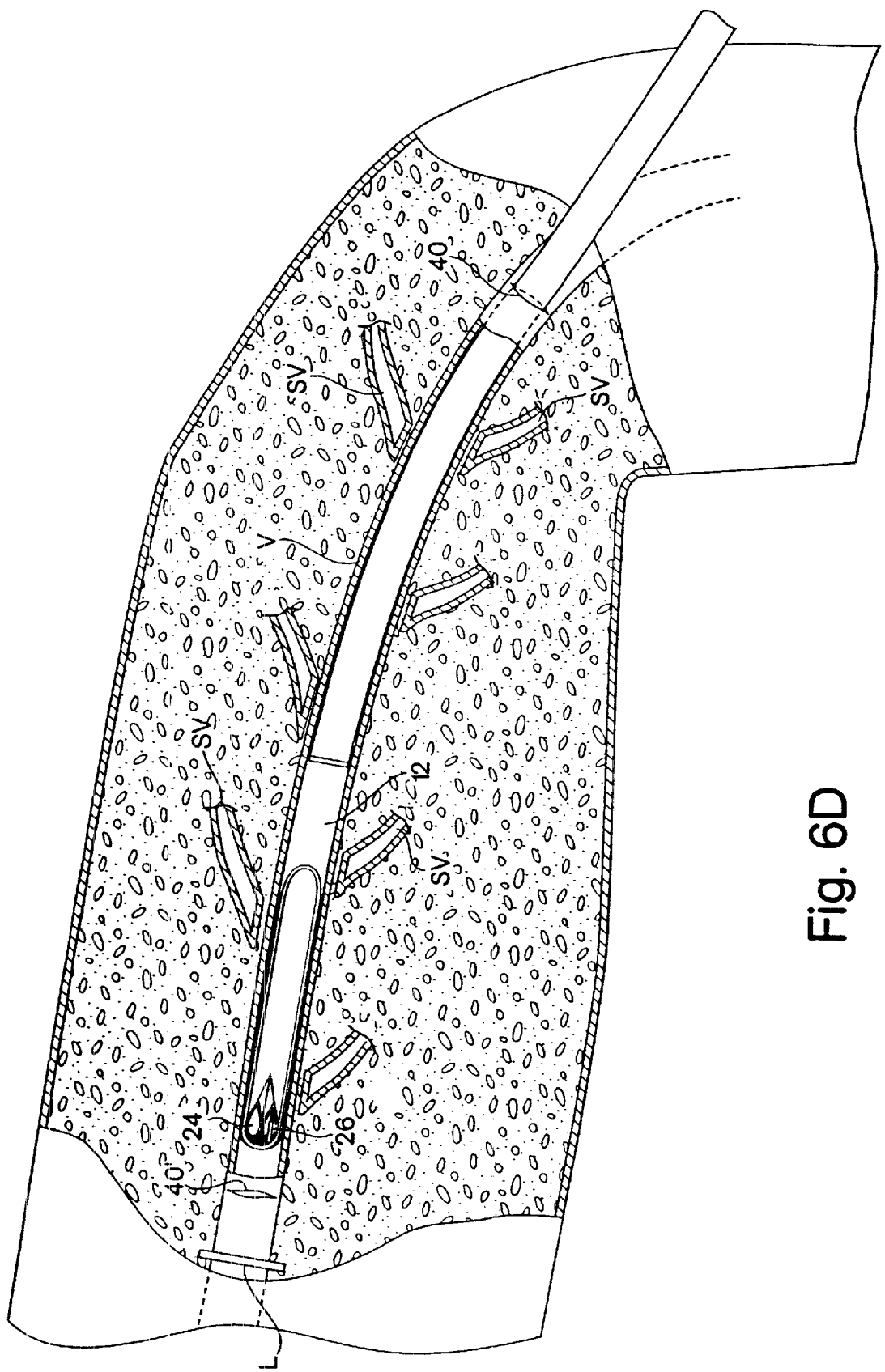
Figure 6E:
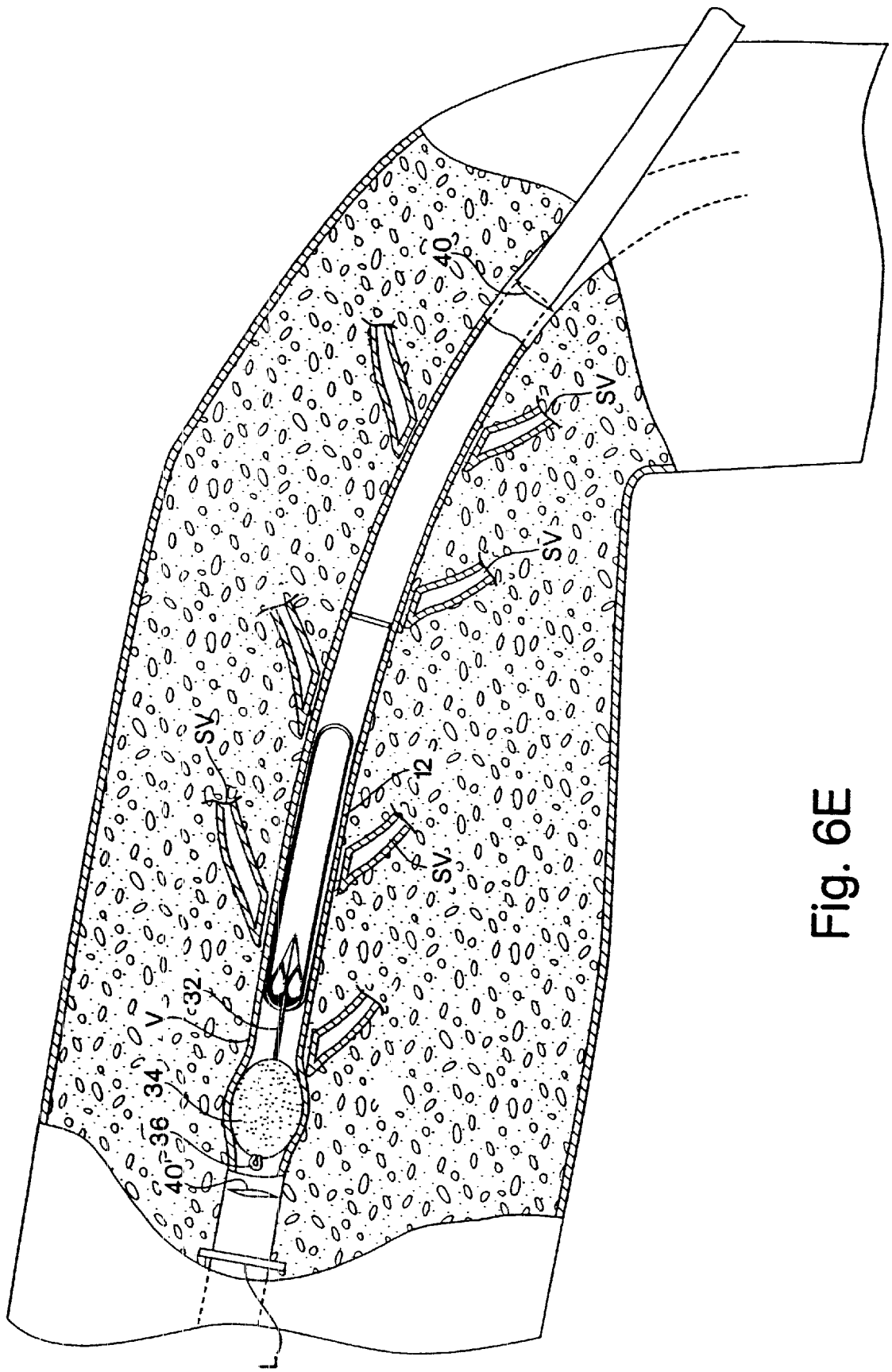

The procedure for removing an elongate vessel are illustrated in FIGS. 6A–6F. The figures demonstrate the removal of the saphenous vein in the leg, however, the invention is similarly employed for removing other vessels. In FIG. 6A, the surgeon makes two small incisions 40 and 40' along the course of the vein V spaced apart the distance along the length of vein to be removed. Blood flow through the vein is disrupted by ligation, clips or the like at the vein ends. In FIG. 6B, the endoscopic guide 12 (and cannulas, if guide is does not have integrated cannulas) is inserted into one incision at the and into vein V. The endoscope 24 (angioscope or fiberoptic device) is inserted into cannula 16 (this step may be done prior to insertion of the guide), and the guide 12 is navigated translumenally through the vein. As the guide 12 moves through the vein, the endoscope 24 provides a means of viewing the interior of the vessel for side branch vessels SV. Because of the beveled end of distal tip 15, the endoscope 24 is free to rotate through a larger visual area within the vein. When junctions of side veins SV are encountered, cautery device 26 is extended through the tool cannula 20 into side vessels. Cautery device 20 is energized and occludes or embolizes the side vessel (FIG. 6C). (The endoscope may be retracted or left in place to view the ligation). The cautery is retracted into tool cannula 20 and the guide proceeds through the vein in this fashion, ligating vessels as necessary (FIG. 6D). Along its path, other tools can be inserted into the tool cannula, such as forceps and valvulotomes, which are manipulated as needed until the guide reaches the opposite incision 40'. In FIG. 6E, phleboextractor 30 is passed through lumen 14 of guide 12, through the distal tip 12A. Inflation media is pumped through tube 32 and expands balloon 34, allowing balloon 34 to frictionally engage and secure the end of the vein segment. Endovascular device 10 is retracted through the vein segment, retracting the vein segment as the device is removed. The surgeon can manipulate harvested vein as it is removed to insure that the vein does gather along the guide as it is removed.

Figure 6F:
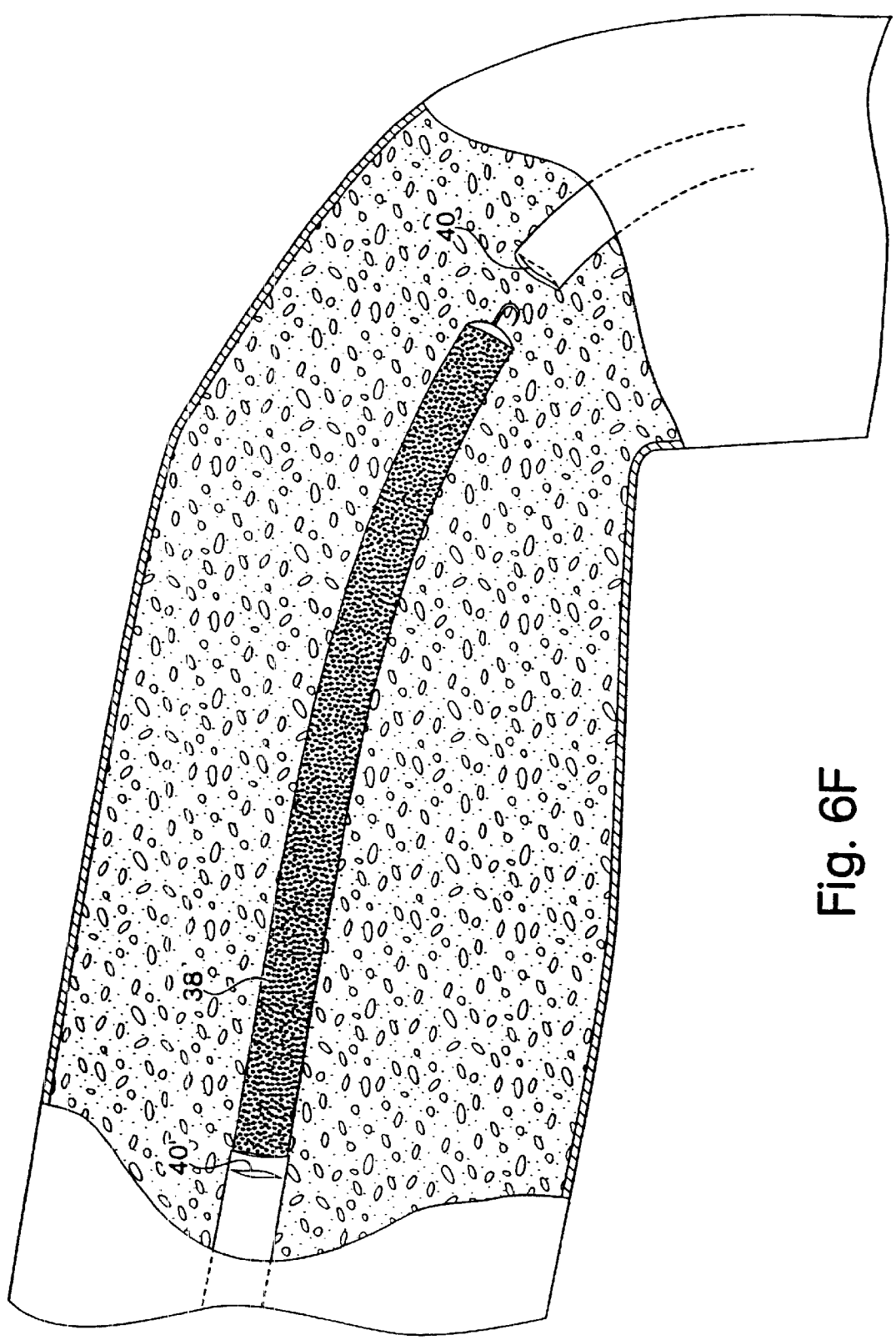

Optionally, prior to device retraction and vein removal, drain 38 is connected to balloon 34 at connecting means 36 and 37. As device 10 is retracted through the vein segment, drain 38 is carried into the space previously occupied by the vein where it can remain for a period of time to supply pharmacological agents or allow drainage of collected blood and fluids (FIG. 6F). After a period of time, drain 38 can be removed from the wound through the incision or be absorbed by the body.

In further embodiments, a visualization device, such as a fiber optic angioscope, can be removably positioned within the drain 38, so that as the drain 38 is drawn (by device 10) into the space previously occupied by the vein, the surgeon can view the region exterior to the distal tip of the guide 12, that is, so that intra-and extra-luminal visualization can occur. The angioscope in the drain 38 can selectively be removed after the drain 38 is fully in place and there is no need to further visualize the surrounding tissue.

Figure 7:
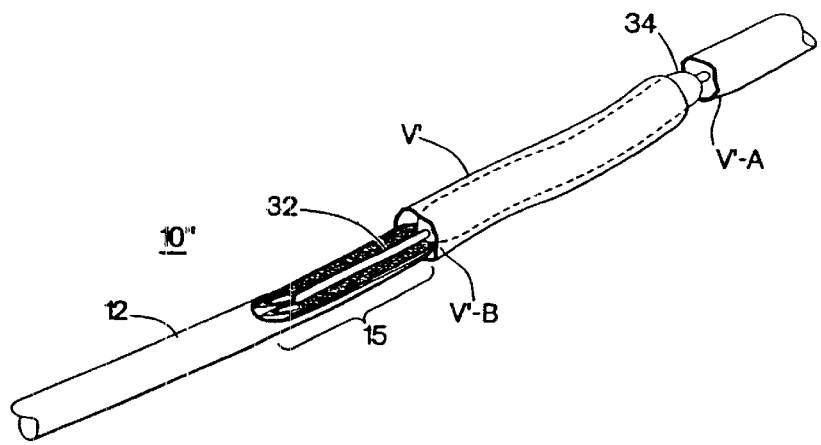
FIG. 7 is a perspective view of the invention configured to harvest a vein segment.

The invention can also be used to harvest segments of vein for use in other areas of the body, such as replacements for diseased coronary arteries. As shown in FIG. 7, in this form of the invention, a guide 12 may include an angioscope (not shown in FIG. 7), a balloon assembly (including balloon 34 and tube 32) and a circumferential vein cutter (not shown in FIG. 7). The balloon 34 has an elongated cylindrical shape (when inflated) with a cross-section diameter substantially that of the vein segment to be harvested. In use, the guide 12 is advanced from an access to the vessel segment (V')-to-be-harvested. The angioscope may be used to inspect the segment V' to confirm that it is suitable for harvest. Then the vein cutter enters the segment V' to its distal V'-A and cuts the vessel segment. Then, the vein cutter is withdrawn and the deflated balloon 34 is advanced within that segment and inflated (to support the segment V'). Then, the vein cutter cuts the segment at its proximal end V'-B to free that segment. Finally, the freed segment may be removed (for example by a small incision in the body) while the inflated balloon maintains the segment V' as a stable condition (so that no damage can occur to the intima of that segment). After removal of the segment V', the guide 12 is withdrawn.

It should be appreciated that by changing the diameter of the guide and cannulas, the device can provide visual access to other anatomical sites in need of visual inspection and endoscopic surgical intervention. Similarly, appropriately sized guides and cannulas allow the device to be used in endovascular surgery for the management of acute arterial occlusions, chronic occlusive artery disease, aneurysmal disease and other vascular traumas. Similarly, when combined with other endoscopic surgical tools, the guide and cannulas can be used for other surgical procedures, such as, for example, endoscopically guided valvulotomies for "in situ" bypass procedures.

The device can also provide assistance in the management of combined endovascular venous and arterial blood flow of liver trauma where the objective is control of massive bleeding and possibly repairing the vascular lesions and hepatic parenchyma. The device can be introduced into both in the portal vein hepatic vein, inferior vena cava as well as the hepatic artery. With the phleboextractor inflated to stop blood flow, the cautery device can cauterize traumatized small vessels, Similarly, fibrin sealants can be introduced to the trauma area through the tool cannula. The biliary tract can be approached in the same fashion in order to repair its lacerated sites.

The invention can also be used for routine venous and or arterial access, for example in central venous pressure monitoring (CVP) monitoring, IV infusion of fluids or arterial lines for monitoring functions such as mean arterial pressure. Similarly, the invention can be used for arterial endoluminal procedures where video-endoscopic access to arterial sites are desired. In such procedures, insertion of arterial lines, IV infusion lines, arterial monitoring devices and cautery devices proceed under direct visualization. For such arterial and venous procedures, smaller diameter guides are used.

As discussed previously, the phleboextractor can be used in conjunction with the mutlilumen guide to excise vessels. It is also contemplated to be within the scope of the invention that the phleboextractor be used to extract vessels without the use of the guide in performing vessel removal procedures. In such procedures, the surgeon makes the necessary incisions in the surgical region of interest as is customary for this type of procedure, such as for a limb, at the ankle and/or knee and groin. The phleboextractor, with the balloon portion in its deflated state, is introduced into one incision, threaded along the vessel segment, to the opposite incision. The balloon portion is inflated to frictionally engage and secure the end of the vein segment. The phleboextractor is retracted along its original path, removing the vein segment as the device is removed.

Figure 8:
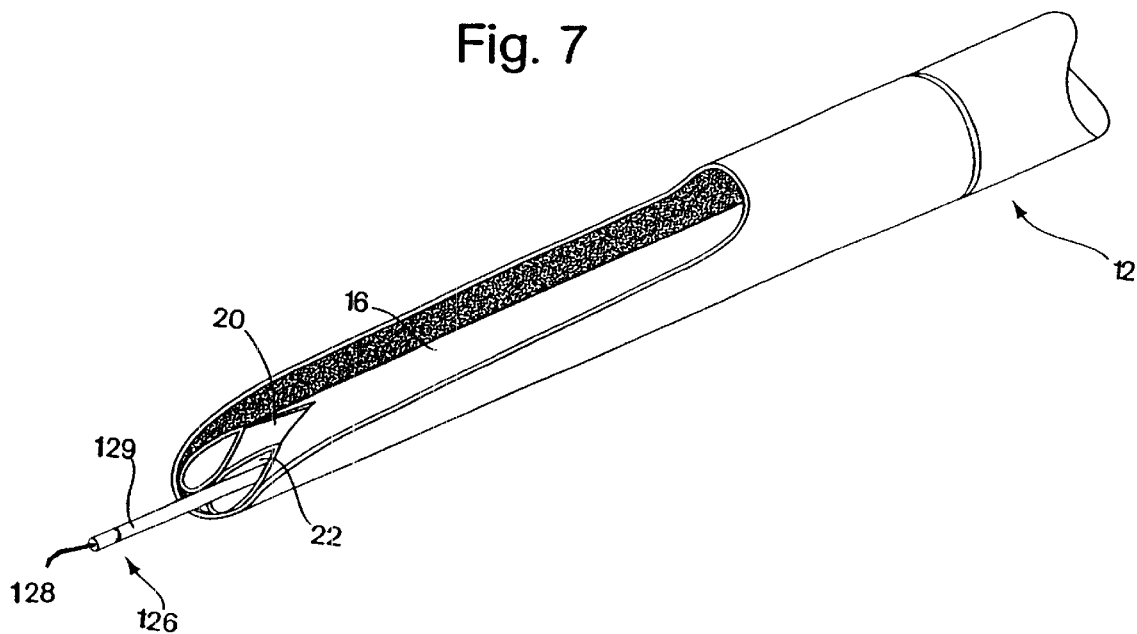
FIG. 8 shows an oblique view of the kit of FIG. 1 showing an intravascular ultrasound device.

In another form of the invention, an intravascular ultrasound (IVUS) device 126 may be used together with the multilumen catheter. In this form, as shown in FIG. 8, a flexible elongated cylindrical element 29, dimensioned to fit within one of the lumens of the catheter 16, is fitted with an ultrasonic transducer 128 at its distal end. Energizing wires (not shown) pass through or along the cylindrical element 129 from the transducer 128 to a proximal end where those wires may be coupled to a conventional ultrasonic driver (not shown). In use, as the distal end of catheter 16 is passed through the vasculature of a patient, the ultrasonic transducer-bearing distal end of the cylindrical element 129 may be advanced through its lumen (22) so that the transducer 128 extends from the distal end of the catheter. The driver may be selectively actuated to cause the transducer 128 to generate ultrasonic energy, which is coupled to adjacent tissue.

Generally, energy is reflected from the tissue back to the transducer 128. At the transducer 128, the energy is converted to electrical signals which are transmitted back to the proximal end of the catheter. At the maximal end, the electrical signals are processed to generate a display representative of the tissue structure near the distal end of the catheter. In one form, the cylindrical element 129 is passive, so that it readily follows the curvature of the lumen 22 within the catheter 16. In alternate embodiments, the cylindrical element 129 may additionally be "steerable", using conventional catheter steering techniques, so that when the distal end (bearing the 128) emerges from the lumen of the distal end of the catheter, the cylindrical element may be offset, via remote control, to effect selective aiming of the transducer toward tissue-to-be-imaged. This guided tip operation may be accomplished with the use of a separate visualizing element (such as a video chip at the end of a flexible rod) passing through another lumen of the multilumen catheter 16, or may be guided using images generated by the ultrasonic transducer 128. The images obtained with this feature of the invention may be used to map the interior of a blood vessel, identify side branch vessels extending from the saphagnous vein, valves, perforations, or other visual features. In practice, the ultrasonic transducer 128 and imaging processor may be of a conventional IVUS type such the CLEAR VIEW ULTRA™ system manufactured by Boston Scientific/Scimed.

The invention may be embodied on other specific form without departing from the spirit or essential characteristics thereof. The present embodiments are therefore to be considered illustrative and not restrictive, the scope of the invention being dictated by the appended claims rather than by the foregoing description, and all changes which come within the meaning and range of equivalency of the claims are therefore intended to be embraced therein.

What is claimed is:

1. A kit for endovascular venous surgery comprising:
   A. an elongated flexible tubular guide extending along a guide axis from a proximal end to a distal end thereof, said tubular guide including at least a first lumen, and a second lumen, each of said lumens extending along a respective one of a first lumen axis and a second lumen axis from said proximal end to said distal end, said first lumen axis and said second lumen axis being substantially parallel to said guide axis,
   B. an angioscope including an elongated flexible image transfer element extending along a scope axis from a proximal end to a distal end thereof, said angioscope being adapted for positioning within said first lumen, whereby said distal end of said image transfer element is adjacent to said distal end of said guide, and whereby said scope axis is substantially parallel to said first lumen axis, and wherein said image transfer element includes means for generating at its proximal end an image representative of a region adjacent to its distal end, and
   C. a phleboextractor adopted for removable insertion into one of said lumens in said guide, said phleboextractor extending between a proximal end and a distal end, and having at said distal end an extractor device having an outer surface for frictionally engaging tissue external to said distal end of said guide when said distal end of said phleboextractor extends beyond said distal end of said guide.

2. A kit according to claim 1 wherein said angioscope is fixedly positioned within said first lumen.

3. A kit according to claim 1 wherein said angioscope is removably positioned within aid first lumen.

4. A kit according to claim 3 wherein said angioscope has an image sensor at said distal end for generating a signal representative of said region, and includes an electrically conductive means for transferring said signal to said proximal end.

5. A kit according to claim 3 wherein said angioscope is an angiofibroscope having a fiber optic bundle extending from said proximal end to said distal end for transferring light from said region to said proximal end, and having a sensor at said proximal end for generating a signal representative of said region from said transferred light.

6. A kit according to claim 5 wherein said fiber optic bundle includes a first portion adapted to transfer light incident on said proximal end to said distal end, and a second portion adapted to transfer light incident on said distal end to said proximal end.

7. A kit according to claim 1 further comprising a cauterizing assembly, including:
   A. an elongated flexible electrically non-conductive sheath having a central lumen, said sheath extending between a proximal end and a distal end, and said sheath being adapted for removable insertion into said second lumen whereby said central lumen extends along an axis substantially parallel to said guide axis,
   B. a flexible elongated electrically conductive cauterizing element extending between a proximal end and a distal end, and adapted for selective insertion into said central lumen whereby said distal end of said cauterizing element extends beyond the end of said sheath and said guide.

8. A kit according to claim 7 wherein said distal end of said cauterizing element has shape memory and is L-shaped when unconstrained, and is constrained to have the shape of said central lumen when therein.

9. A kit according to claim 8 wherein the angular orientation of said distal tip of said cauterizing element about an axis parallel to said guide axis is controllable from said proximal end of said guide.

10. A kit according to claim 7 wherein said sheath at its distal end includes a deflector adapted to define an exit path for the distal end of said cauterizing element extending from said distal end of said sheath along a path (P) angularly displaced from said central lumen by a non-zero angle (A).

11. A kit according to claim 10 wherein the angular orientation of said path about an axis parallel to said guide axis in controllable from said proximal end of said guide.

12. A kit according to claim 1 wherein said extractor device is a rigid detachable element coupled to said phleboextractor.

13. A kit according to claim 1 wherein said extractor device is an inflatable/deflatable balloon, adapted for inflation/deflation from said proximal end of said phleboextractor.

14. A kit according to claim 13 wherein said balloon is elastic.

15. A kit according to claim 14 wherein said balloon has a rough outer surface adapted for frictional engagement with tissue.

16. A kit according to claim 13 wherein said balloon is inelastic.

17. A kit according to claim 13 wherein said balloon has a rough outer surface adapted for frictional engagement with tissue.

18. A kit according to claim 1 further comprising a permeable flexible tube including a selectively operable means for coupling an end of said tube to said extractor device.

19. A kit according to claim 1 wherein said distal end of said guide is beveled.

20. A kit according to claim 1 wherein said guide has an outer diameter in the approximate range 4–8 mm.

21. A kit according to claim 1 further comprising an intravenous ultrasound device.

22. A kit according to claim 21 wherein said intravenous ultrasound device includes an elongated flexible cylindrical element extending between proximal and distal ends thereof, and including an ultrasonic transducer at said distal end.

23. A device for removing a vein segment, comprising:
a phleboextractor adapted for removable insertion into a vein, said phleboextractor extending between a proximal end and a distal end, and having at said distal end an extractor device for frictionally engaging tissue external to said distal end.

24. A device according to claim 23 wherein said extractor device is a rigid detachable element coupled to said phleboextractor.

25. A device according to claim 23 wherein said extractor device is an inflatable/deflatable balloon, adapted for inflation/deflation from said proximal end of said phleboextractor.

26. A device according to claim 25 wherein said balloon is elastic.

27. A device according to claim 26 wherein said balloon has a rough outer surface adapted for frictional engagement with tissue.

28. A device according to claim 26 wherein said balloon is inelastic.

29. A device according to claim 25 wherein said balloon has a rough outer surface adapted for frictional engagement with tissue.

30. A device according to claim 23 further comprising a permeable flexible tube including a selectively operable means for coupling an end of said tube to said extractor device.

* * * * *

UNITED STATES PATENT AND TRADEMARK OFFICE
CERTIFICATE OF CORRECTION

PATENT NO. : 6,520,975 B2
DATED : February 18, 2003
INVENTOR(S) : Antônio Carlos Netto da Silva Branco It is certified that error appears in the above-identified patent and that said Letters Patent is hereby corrected as shown below:

<u>Title page,</u>
Item [76], Inventor, should read: -- Antônio Carlos Netto da Silva Branco, R. Dr. José Augusto de Queiroz, 256, São Paulo, CEP 05670-030 (BR) --

<u>Column 2,</u>
Lines 14 through 54, delete the following paragraphs from the "BACKGROUND OF THE INVENTION".

" In one form, the kit also provides a cautery device that extends through one lumen provided within the guide. The preferred cautery device includes an elongated flexible electrically non-conductive tubular sheath which surrounds a flexible elongated electrically conductive cauterizing element. Under operator control, the cauterizing element may be driven to extend beyond the end of the sheath and the guide. In one form, the cauterizing element has shape memory and is L-shaped when unconstrained, and is constrained to have the shape of one of the sheaths when retracted therein. Alternately, the sheath may have a deflector surface at its exit to direct the cauterizing element (and the sheath, in some forms) along a path angularly offset from the principal axis of the guide.

The orientation of the cauterizing element about the sheath axis is operator controllable from the proximal end of the guide. With this configuration, selective cauterization of branch vessels may be effected.

The kit further includes an elongated phleboextractor extending between a proximal end and a digital end thereof. The phleboextractor is insertable through a lumen of the guide, and has an extractor device at its distal end. The extractor device is adapted for frictionally engaging tissue external to the end of the guide when the distal end of the phleboextractor extends beyond the distal end of the guide. The extractor device can be a balloon which can be selectively inflated to a shape having a diameter greater than that of the guide and deflated. The balloon may be elastic or inelastic. The outer surface of the balloon can be smooth, roughened or possess regions of both types of surfaces to provide secure engagement between the balloon and surrounding tissue. The phleboextractor is adapted so that upon deployment with its distal end beyond the guide, and its balloon inflated, the proximal end of the phleboextractor may be pulled from the first incision at the proximal end of the guide, with its distal end (and the extractor) device dragging with it the vein segment.

The kit may further include tubular a drain of porous flexible material which is adapted to be inserted into the second incision and connected to the phleboextractor at its distal end and be drawn into the surgical area as the "

UNITED STATES PATENT AND TRADEMARK OFFICE
CERTIFICATE OF CORRECTION

PATENT NO.     : 6,520,975 B2                                                   Page 2 of 3
DATED          : February 18, 2003
INVENTOR(S)    : Antônio Carlos Netto da Silva Branco It is certified that error appears in the above-identified patent and that said Letters Patent is hereby corrected as shown below:

<u>Column 3,</u>
Line 18, after "representative", delete ".";
Line 26, after "optic viewing device", delete "phleboextractor is withdrawn through the first incision. The drain can be infused with pharmacological agents or collect wound drainage.";
Line 26, after "optic viewing device." insert paragraphs listed below:

-- In one form, the kit also provides a cautery device that extends through one lumen provided within the guide. The preferred cautery device includes an elongated flexible electrically non-conductive tubular sheath which surrounds a flexible elongated electrically conductive cauterizing element. Under operator control, the cauterizing element may be driven to extend beyond the end of the sheath and the guide. In one form, the cauterizing element has shape memory and is L-shaped when unconstrained, and is constrained to have the shape of one of the sheaths when retracted therein. Alternately, the sheath may have a deflector surface at its exit to direct the cauterizing element (and the sheath, in some forms) along a path angularly offset from the principal axis of the guide. The orientation of the cauterizing element about the sheath axis is operator controllable from the proximal end of the guide. With this configuration, selective cauterization of branch vessels may be effected.

The kit further includes an elongated phleboextractor extending between a proximal end and a digital end thereof. The phleboextractor is insertable through a lumen of the guide, and has an extractor device at its distal end. The extractor device is adapted for frictionally engaging tissue external to the end of the guide when the distal end of the phleboextractor extends beyond the distal end of the guide. The extractor device can be a balloon which can be selectively inflated to a shape having a diameter greater than that of the guide and deflated. The balloon may be elastic or inelastic. The outer surface of the balloon can be smooth, roughened or possess regions of both types of surfaces to provide secure engagement between the balloon and surrounding tissue. The phleboextractor is adapted so that upon deployment with its distal end beyond the guide, and its balloon inflated, the proximal end of the phleboextractor may be pulled from the first incision at the proximal end of the guide, with its distal end (and the extractor) device dragging with it the vein segment.

The kit may further include tubular a drain of porous flexible material which is adapted to be inserted into the second incision and connected to the phleboextractor at its distal end and be drawn into the surgical area as the phleboextractor is withdrawn through the first incision. The drain can be infused with pharmacological agents or collect wound drainage.--

UNITED STATES PATENT AND TRADEMARK OFFICE
CERTIFICATE OF CORRECTION

PATENT NO. : 6,520,975 B2
DATED : February 18, 2003
INVENTOR(S) : Antônio Carlos Netto da Silva Branco It is certified that error appears in the above-identified patent and that said Letters Patent is hereby corrected as shown below:

Column 6,
Line 34, after "and", delete "detachaly" and insert therefor -- detachably --.

Column 10,
Line 16, after "within", delete "aid" and insert therefor -- said --.

Signed and Sealed this

Nineteenth Day of August, 2003

JAMES E. ROGAN
*Director of the United States Patent and Trademark Office*